(12) United States Patent
Leuthold et al.

(10) Patent No.: US 11,931,733 B2
(45) Date of Patent: Mar. 19, 2024

(54) DEVICE AND METHOD FOR REPEATEDLY MODIFYING THE COMPOSITION OF A FLUID

(71) Applicant: Sartorius Stedim Biotech GmbH, Goettingen (DE)

(72) Inventors: Martin Leuthold, Goettingen (DE); Alexander Helling, Ebergoetzen (DE); Ulrich Grummert, Bad Sooden-Allendorf (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 0 days.

(21) Appl. No.: 17/339,891

(22) Filed: Jun. 4, 2021

(65) Prior Publication Data
US 2021/0291161 A1    Sep. 23, 2021

Related U.S. Application Data

(63) Continuation of application No. PCT/EP2019/083797, filed on Dec. 5, 2019.

(30) Foreign Application Priority Data

Dec. 7, 2018   (DE) .................... 10 2018 009 597.6

(51) Int. Cl.
*B01L 3/00* (2006.01)
*B01D 61/14* (2006.01)
*G05D 21/00* (2006.01)

(52) U.S. Cl.
CPC ............ *B01L 3/502* (2013.01); *B01D 61/146* (2022.08); *G05D 21/00* (2013.01);
(Continued)

(58) Field of Classification Search
CPC ............ B01L 3/502; B01L 2200/0631; B01L 2300/0663; B01L 2300/0681;
(Continued)

(56) References Cited

U.S. PATENT DOCUMENTS 10,022,463 B2   7/2018  Lobedann et al.
10,434,201 B2   10/2019 Schwan et al.
(Continued)

FOREIGN PATENT DOCUMENTS

DE   102016004115 A1   10/2017
EP       3116552         1/2017
(Continued)

OTHER PUBLICATIONS

International Search Report, PCT/EP2019/083797, dated Feb. 7, 2020, 2 pages.
(Continued)

*Primary Examiner* — Benjamin R Whatley
*Assistant Examiner* — Jacqueline Brazin
(74) *Attorney, Agent, or Firm* — Edell, Shapiro & Finnan, LLC (57) ABSTRACT

A device and a method for repeatedly modifying the composition of a fluid. The device includes a first module (19) modifying the composition of the fluid, a second module (21) modifying the composition of the fluid and a dwell module (20) with an inlet (8) and an outlet (10). The first module is connected in a fluid-conducting manner to the dwell module inlet and the dwell module outlet is connected in a fluid-conducting manner to the second module. Either the first or the second module is a filter unit, or the first module is a first filter unit and the second module is a second filter unit. The filter unit(s) include(s) at least one first filter medium (4, 14) delimiting a supply channel (2, 12) and a retentate channel (1, 11) and at least one second filter
(Continued)

medium (5, 15) delimiting the retentate channel and a permeate channel (3, 13).

18 Claims, 3 Drawing Sheets

(52) U.S. Cl.
CPC .............. *B01L 2200/0631* (2013.01); *B01L 2300/0663* (2013.01); *B01L 2300/0681* (2013.01); *B01L 2400/06* (2013.01)

(58) Field of Classification Search
CPC ..... B01L 2400/06; G05D 21/00; A23C 9/142; C07K 1/34; B01D 2311/18; B01D 61/16; B01D 2313/50; B01D 2317/022; B01D 2317/06; B01D 2317/08; B01D 2319/022; B01D 2319/06; B01D 61/142; B01D 61/18; B01D 61/145
USPC ........................................................ 210/743
See application file for complete search history.

(56) References Cited

U.S. PATENT DOCUMENTS

| | | | |
|---|---|---|---|
| 2007/0246406 A1 | 10/2007 | Dibel et al. | |
| 2008/0237110 A1* | 10/2008 | Lightfoot | B01D 61/58 210/641 |
| 2013/0245139 A1* | 9/2013 | Kozlov | B01J 39/26 530/413 |
| 2016/0375190 A1* | 12/2016 | Blatter | A61M 1/1678 604/28 |
| 2017/0340795 A1 | 11/2017 | Charest et al. | |
| 2019/0022654 A1* | 1/2019 | Hammerschmidt | B01F 25/45241 |
| 2019/0030486 A1 | 1/2019 | Leuthold et al. | |
| 2019/0381457 A1* | 12/2019 | Erdenberger | B01D 61/246 |

FOREIGN PATENT DOCUMENTS

| | | | | |
|---|---|---|---|---|
| EP | 3288596 B1 | 3/2019 | | |
| WO | WO-2008127087 A1 * | 10/2008 | ......... | B01D 15/1807 |
| WO | 2009129226 A1 | 10/2009 | | |
| WO | 2015135844 A1 | 9/2015 | | |
| WO | 2017174192 A1 | 10/2017 | | |
| WO | 2018039163 A1 | 3/2018 | | |

OTHER PUBLICATIONS

Shrestha "Characterization of Porous Membranes Via Porometry", (2012), 103 pages.

Davila "Characterization of Ultra and Nanofiltration Commercial Filters by Liquid-Liquid Displacement Porosimetry", (2013), 133 pages.

Reingruber et al., "Quantitative characterization of microfiltration membranes by 3D reconstruction", Journal of Membrane Science, 372 (2011) 66-74, also in Fuel and Energy Abstracts Apr. 2011, 10 pages.

Korean Office Action with English translation, KR Application No. 10-2021-7015507, dated Dec. 12, 2022, 9 pages.

* cited by examiner

DEVICE AND METHOD FOR REPEATEDLY MODIFYING THE COMPOSITION OF A FLUID

CROSS REFERENCE TO RELATED APPLICATIONS

This is a Continuation of International Application PCT/EP2019/083797 which has an international filing date of Dec. 5, 2019, and the disclosure of which is incorporated in its entirety into the present Continuation by reference. This Continuation also claims foreign priority under 35 U.S.C. § 119(a)-(d) to and also incorporates by reference, in its entirety, German Patent Application 10 2018 009 597.6 filed on Dec. 7, 2018.

FIELD OF INVENTION

The present invention relates to a device and a method for modifying the composition of a fluid more than once, i.e., repeatedly.

BACKGROUND

In many processes it is necessary to modify the composition of a fluid repeatedly. In existing methods, however, a volume change in the fluid may be required for this, which can make the process management more difficult. It is, however, desirable to be able to modify the volume of the fluid in the process as desired. In addition, with conventional methods, the simultaneous separation of contaminants involves an increased effort.

DE 10 2016 004 115 A1 discloses a crossflow filtration unit for continuous diafiltration.

WO 2018/039163 A1 discloses a method of purifying a heterologous protein from egg white.

EP 3 116 552 A1 discloses a device and a method for continuous virus inactivation.

EP 3 288 596 B1 discloses a method for continuous virus inactivation in a microreactor.

SUMMARY

It is thus an object of the present invention to provide a device and a method which enable a gentle repeated modification of the composition of a fluid while simultaneously removing contaminants without imposing restrictions with respect to volume changes in the fluid.

The above object is achieved with the embodiments characterized in the claims.

In a first aspect, the present invention relates to a device for repeatedly modifying the composition of a fluid, comprising a first module for modifying the composition of the fluid, a second module for modifying the composition of the fluid and a dwell module with an inlet and an outlet. The first module is connected in a fluid-conducting manner to the inlet of the dwell module and the outlet of the dwell module is connected in a fluid-conducting manner to the second module. The first module or the second module is a filter unit, or the first module is a first filter unit and the second module is a second filter unit. The filter unit and/or filter units each have at least one supply channel, at least one first filter medium, at least one retentate channel, at least one second filter medium and at least one permeate channel, arranged so that the first filter medium delimits the supply channel and the retentate channel from one another and the second filter medium delimits the retentate channel and the permeate channel from one another. The supply channel is connected in a fluid-conducting manner to at least one inlet for a supply medium, the retentate channel is connected in a fluid-conducting manner to at least one inlet for the fluid and to at least one outlet for the fluid, and the permeate channel is connected in a fluid-conducting manner to at least one outlet for a permeate.

The device according to the invention enables the composition of a fluid to be modified repeatedly in a gentle manner and simultaneously for contaminants in the fluid to be separated out. In particular, the device and the method according to the invention are suitable for modifying the composition of a fluid for a period that can be monitored. In addition, with the modifications of the composition, the volume of the fluid can also be adjusted simultaneously. The device and the method according to the invention are also suitable for a continuous mode of operation.

According to the invention, a fluid should be understood as a liquid or gaseous mixture or a liquid or gaseous compound. For example, a buffer solution represents a fluid. A culture medium or its liquid and/or gaseous components can also be a fluid.

According to the present invention, at least one of the first and the second modules is the filter unit defined above. Furthermore, the first and the second module are not subject to any particular restriction. This means that any device suitable for modifying the composition of a fluid can be used.

According to a preferred embodiment of the present invention, the first or second module is a static mixer. The necessity for conducting away a permeate stream is dispensed with for the module, which is a static mixer, so that the method can be carried out more easily and is particularly economical. The above preferred embodiment comprises the case wherein the first module is a static mixer and the second module is the filter unit and the case wherein the first module is the filter unit and the second module is a static mixer. It is often the case that the first module is a static mixer and the second module is the filter unit.

According to a further preferred embodiment of the present invention, the first or second module is the filter unit described above with a first and a second filter medium and the second or the first module is a further filter unit having at least one filter medium. Preferably, the further filter unit has a single filter medium. The further filter unit can be, for example, a sterile filter. Preferably, the further filter unit has only one inlet and only one outlet (a dead-end filter). It is preferable that the first module is the filter unit described above with a first and a second filter medium and the second module is the further filter unit having at least one filter medium. With a device of this embodiment according to the invention, for example, a precipitation reaction can be initiated with the first module, whereby the precipitation reaction can take place in the dwell module and the further filter unit can separate out the precipitation product.

According to a further preferred embodiment of the present invention, the first or second module is the filter unit described above with a first and a second filter medium and the second or the first module is a further filter unit having at least one supply channel, at least one filter medium and at least one retentate channel, arranged such that the filter medium delimits the supply channel and the retentate channel from one another, the supply channel being connected in a fluid-conducting manner to at least one inlet for a supply medium and the retentate channel being connected in a fluid-conducting manner to at least one inlet for the fluid and to at least one outlet for the fluid. The filter unit with the filter medium is constructed like the filter unit described above with the first and the second filter medium, with the provision that the second filter medium and the permeate channel and its outlet are lacking. For this further filter unit, the statements in relation to the filter unit with the first and second filter medium apply accordingly. The further filter unit can then be used, in particular, if the volume of the fluid through the first or the second module is not to be monitored. According to this embodiment with the filter unit with the filter medium, for example, a dilution can be carried out.

According to a further preferred embodiment of the present invention, the first or second module is the filter unit described above with a first and a second filter medium and the second or the first module is a further filter unit having at least one retentate channel, at least one filter medium and at least one permeate channel, arranged such that the filter medium delimits the retentate channel and the permeate channel from one another, the retentate channel being connected in a fluid-conducting manner to at least one inlet for the fluid and to at least one outlet for the fluid and the permeate channel being connected in a fluid-conducting manner to at least one outlet for the permeate. The filter unit with the filter medium is constructed like the filter unit described above with the first and the second filter medium, with the provision that the first filter medium and the supply channel and its inlet are lacking. For this further filter unit, the statements in relation to the filter unit with the first and second filter medium apply accordingly. The further filter unit can then be used, in particular, if the volume of the fluid through the first or the second module is not to be monitored. According to this embodiment with the further filter unit with the filter medium, for example, a precipitation product can be separated out.

According to a further preferred embodiment of the present invention, the first or the second module is the filter unit described above with the first and the second filter medium and the second or the first module is a membrane adsorber. Preferably, the first module is a membrane adsorber and the second module is the filter unit with a first and a second filter medium. In this case, the membrane adsorber can firstly be laden with a product (e.g. monoclonal antibodies, protein). For this purpose, a loading medium which contains the product is firstly fed to the membrane adsorber. Accordingly, the product contained in the loading medium is adsorbed by the membrane adsorber. The loading medium can leave the device according to the invention by way of the dwell module and the second module (filter unit). Preferably, a valve is mounted on the outlet of the membrane adsorber so that the loading medium can be conducted away therethrough without having to pass through the dwell module and the second module. Once the loading medium has been conducted away, the fluid can be fed in as the eluent, so that the membrane adsorber releases to the fluid the product adsorbed on it. In this case, the fluid which is fed to the membrane adsorber preferably has a pH value of less than 7, particularly preferably from 2 to 6, more particularly preferably from 3 to 5. This permits viruses contained in the fluid to be inactivated.

According to a further preferred embodiment of the present invention, in place of a membrane adsorber, a chromatography module which contains a chromatography medium can be used. The chromatography medium can be, for example, a gel or a monolith. The statements above relating to the embodiment with a membrane adsorber apply accordingly for the embodiment with a chromatography module.

According to a further preferred embodiment of the present invention, the first module is a first filter unit and the second module is a second filter unit. In this way, a particularly gentle repeated composition modification can be achieved. In addition, the volume of the fluid can be adjusted both by the first module and also by the second module. Equally, this preferred embodiment enables contaminants to be removed particularly effectively.

The device according to the invention can be provided with sensors. Suitable sensors include sensors for measuring pH value (pH sensors), conductivity, pressure and flow rate, as well as spectroscopic sensors (for UV, UV/Vis, IR, NIR spectroscopy and Raman spectroscopy).

The sensors serve for monitoring and controlling the method according to the invention. Preferably, sensors are mounted on the outlet of the retentate channel, for instance pH sensors. In this way, the composition or other properties of the fluid can be measured on leaving the filter unit of the first and/or second module.

The device according to the invention can have valves and/or pumps. The substance streams of the fluid of the supply medium and of the permeate can be controlled with the valves and/or pumps. Suitable valves are, for example, pinch valves and needle valves. Preferably, a valve or a pump is mounted on the outlet of the retentate channel. The filtration pressure within the retentate channel and thus the volumetric flow rate through the second filter medium can be adjusted with the valve and/or the pump. Independently thereof, it is preferable that the outlet of the permeate channel has a valve. By use of the valve on its outlet, the permeate channel can be closed. This can be helpful if, in the filtration unit, only a combining of the supply medium and of the fluid is desired, without a filtration being performed by the second filter medium.

The filter unit(s) with the first and the second filter medium can be supplied with inserts in the retentate channel, the supply channel and the permeate channel and preferably in the retentate channel. Inserts of this type are suitable for keeping the retentate channel, the supply channel and the permeate channel open and/or for ensuring an optimum mixing in the respective channel. The inserts can consist, for example, of a textile material (e.g. a woven or knitted fabric and/or a nonwoven fabric).

According to the invention, the dwell module is not subject to any special restriction provided it is suitable for accepting a fluid and discharging it again. The duration between the composition modification in the first module and the composition modification in the second module can be adjusted through the size and the design of the dwell module. The dwell module can be, for example, a container with an inlet and an outlet. A specific example of the dwell module is a stirrer vessel with an inlet for feeding in the fluid and an outlet for conducting it away.

According to a preferred embodiment of the present invention, the dwell module is configured so that the dwell time of the fluid in the dwell module is from 1 minute to 24 hours, preferably from 5 minutes to 2 hours, more preferably from 10 minutes to 1 hour.

The dwell module preferably defines a fluid path. A fluid path is a volume through which the fluid can flow, provided it is situated in the dwell module. A dwell module which defines a fluid path can be, for example, a tube or a hose. In this case, similarly to a tubular flow reactor, one end of the tube or hose forms the inlet, the other end forms the outlet of the dwell module.

The fluid path can have, for example, one or more meandering channels and/or one or more spiral-shaped channels. The one or more channels can be introduced, for example, by impressing, milling and/or injection molding into a plastics surface or provided by a correspondingly formed hose and/or a correspondingly formed tube.

According to a preferred embodiment of the present invention, the dwell module comprises a coherent volume which is subdivided by at least one subdividing element. A volume that is subdivided and coherent in this way defines a fluid path through which the fluid can flow. The at least one subdividing element can consist, for example, of a plurality of deflector plates and/or deflector films.

When deflector films are used, spacers are preferably inserted between the deflector films. This permits the mechanical stability and/or immovability of the deflector films to be enhanced. A textile material (e.g. a woven or knitted fabric and/or a nonwoven fabric) is preferably used as spacers. With a textile material, a thorough mixing of the fluid can be ensured and the occurrence of regions with laminar flow can be reduced. A spacer/textile material can also be introduced into the fluid path which is preferably defined by the dwell module if no deflector plates or films are installed.

According to a further preferred embodiment of the present invention, the dwell module comprises a plurality of parallel flow channels. Each of the parallel flow channels is connectable to a common inlet and to a common outlet for the fluid. In this way, one or more of the parallel flow channels can be connected to the common inlet and outlet (fluid flows through the connected flow channel) or can be blocked by the common inlet and outlet (no fluid flows through the blocked flow channel). It is thus possible to modify the number of the parallel flow channels through which the fluid flows, so that the dwell time of the fluid in the dwell module can be regulated. The connectability of the parallel flow channels to the common inlet and to the common outlet for the fluid can be ensured, for example, with the aid of valves.

A further dwell module can possibly be connected to the second module, said dwell module being connected in a fluid-conducting manner to an outlet of the second module. A third module which can be constructed like the first and/or second module can be connected in a fluid-conducting manner to the outlet of the further dwell module. With an arrangement of this type, a cascade of modules for composition modification, and dwell modules, by which the composition of the fluid can be modified more than twice can be constructed.

The device according to the invention can have more than one first module, more than one second module and/or more than one dwell module. This means that the device according to the invention can have two or more first modules, two or more second modules and/or two or more dwell modules. With such parallelizing, the throughput of the first module, the second module and/or the dwell module can be adapted.

In the device according to the invention, the first module is connected in a fluid-conducting manner to the inlet of the dwell module. In addition, the outlet of the dwell module is connected in a fluid-conducting manner to the second module. The first module can thereby be directly connected (i.e. without any intermediate connection) to the inlet of the dwell module or by way of an intermediate connection, for example, via a pipeline or a hose. The same applies for the connection between the outlet of the dwell module and the second module. With a direct connection, a compact construction of the device according to the invention can be realized. If an intermediate connection is used, the device according to the invention can easily be assembled from the first and second modules and the dwell module and, if needed, combined with modules of different design.

If the first module is a filter unit as described above, having a first and a second filter medium, then the outlet of the retentate channel of the first module is connected in a fluid-conducting manner to the inlet of the dwell module. If the second module is a filter unit as described above, having a first and a second filter medium, then the outlet of the dwell module is connected in a fluid-conducting manner to the inlet of the retentate channel of the second module.

According to the present invention, the device comprises, as the first and/or the second module, the filter unit described above with a first and a second filter medium. Herein, statements relating to such filter units apply both for the case that the first and the second module are such filter units and also for the case that only one of the first and the second module is such a filter unit.

According to a preferred embodiment of the present invention, the filter unit is a flat filter module, a spiral-wound fiber module or a hollow fiber module, whereby a flat filter module is preferred. If the filter unit is configured as a flat filter module, the first filter medium and the second filter medium have a flat shape. The expression "flat" indicates that the respective filter medium (filter material) lies substantially in a single plane. Preferably all the filter media substantially lie in planes that are largely parallel to one another. The filter media that are suitable according to the invention are not subject to any particular restriction and can be, for example, ceramic membranes, nonwoven textiles and polymer membranes.

The first and second filter media are suitable for filtration of the supply medium and the fluid. The first filter medium and the second filter medium are at least partially permeable to the supply medium and the fluid.

According to a preferred embodiment, at least the second filter medium is not permeable to one or more of the products possibly contained in the fluid. In this way, it is prevented that products possibly contained in the fluid pass from the retentate channel into the permeate channel. Preferably, the first filter medium is also not permeable to the products possibly contained in the fluid. As described in greater detail below, the products can be, for example, an antibody.

The first filter medium and the second filter medium preferably each have a pore size, independently of one another, from 0.5 nm to 1 mm, particularly preferably from 1 nm to 10 µm, particularly preferably from 2 nm to 100 nm. "Independently of one another" means in this context that the first and the second filter medium do not have to have the same pore size and/or material properties.

In order to determine the pore size, according to the invention, at pore sizes of at least 0.1 µm, i.e. for microfiltration membranes with a mean pore size from 0.1 to 10 µm, capillary flow porometry is used. This involves a gas/liquid porosimetry, in which the differential gas pressure levels and flow rates are measured with a membrane sample first in the moist state and then in the dry state. Before the measurement, the membrane sample is brought into contact with a wetting liquid in such a way that all of the pores present are filled with this liquid. After filling the pores and introducing the sample, the measuring cell is to be closed and the measurement started. The gas pressure is increased automatically and incrementally after the start of the measurement and the pore diameters corresponding to the applied pressure are emptied by the gas pressure. This process takes place until the relevant pore region has been detected, i.e., until even the smallest pores present in the measuring region are freed of the liquid. Thereafter, the pressure is lowered again and the measurement is repeated automatically on the now dry sample. The difference between the two pressure/flow rate curves is used to calculate the pore size distribution using the Young Laplace equation (see also A. Shrestha, "Characterization of porous membranes via porometry", 2012, Mechanical Engineering Graduate Theses & Dissertations, Paper 38, University of Colorado at Boulder).

In order to determine pore sizes of more than 10 µm to 1 mm, the method described in the Journal of Membrane Science 372 (2011), pages 66 to 74 based on image analysis can be used.

For pore sizes of less than 0.1 µm, according to the invention, the liquid-liquid displacement method is used. This method has similarities with capillary flow porometry. However, in this case it is not the gas flow rates, but rather the flow rates of the displacing liquid that are measured as a function of the differential pressure increase (see also R. Dávila, "Characterization of ultra and nanofiltration commercial filters by liquid-liquid displacement porosimetry", 2013).

According to a preferred embodiment of the invention, the first filter medium is a first filtration membrane. The second filter medium is preferably a second filtration membrane. It is particularly preferred that the first filter medium is a first filtration membrane and that the second filter medium is a second filtration membrane. The filtration membranes can be made, for example, of polyvinylidene fluoride, cellulose and derivatives thereof, polyethersulfone (PES) or polysulfone, whereby cross-linked cellulose hydrate is particularly preferred.

The device according to the invention is suitable for all uses in which the composition of a fluid must be modified repeatedly. In particular, the device according to the invention is suitable for virus inactivation.

The statements below relating to the method according to the invention apply mutatis mutandis to the device according to the invention.

In a further aspect, the present invention relates to a method for repeatedly modifying the composition of a fluid, comprising (a) providing the device according to the invention described above; (b) feeding the fluid into the first module; and (c) conducting away the fluid from the second module, wherein step (b) and/or step (c) comprises/comprise the following steps: (i) feeding the supply medium into the inlet for the supply medium; (ii) feeding the fluid into the inlet for the fluid; (iii) conducting away the fluid from the outlet for the fluid; and (iv) conducting away the permeate from the outlet for the permeate. Since in the device according to the invention, the first module is connected in a fluid-conducting manner to the inlet of the dwell module and the outlet of the dwell module is connected in a fluid-conducting manner to the second module, in the method according to the invention, the fluid flows firstly through the first module, then through the dwell module, and finally through the second module.

The statements above relating to the method according to the invention apply mutatis mutandis to the device according to the invention.

The method according to the invention is suitable for any desired uses in which repeatedly modifying the composition of a fluid is required. It is possible, for example, in the first module to bring the fluid into contact with a reagent in order to initiate a chemical reaction, to let the chemical reaction run in the dwell module and in the second module to interrupt (quench) the reaction, for example, by adding a further reagent.

With steps (i) to (iv) of the method according to the invention, at the same time, a gentle modification to the composition of the fluid can be achieved, as well as a separation of contaminants from the fluid. The second filter medium can be selected so that any contaminants possibly contained in the fluid pass through the second filter medium to be conducted away as components of the permeate, wherein desired products (e.g. monoclonal antibodies) remain in the fluid since they cannot pass through the second filter material. Alternatively, the second filter medium can be selected so that it cannot be passed through by undesirable contaminants. In this case, the second filter medium can be passed through by the product. In this case, the undesirable contaminants remain in the fluid. This means that the permeate can be and/or contain the desired product at the end of the method.

The method according to the invention is particularly suitable for initiating a precipitation reaction by modifying the composition in the first module, allowing the precipitation reaction to proceed in the dwell module and, in the second module, separating the precipitation product, for example, by filtration.

Furthermore, the method according to the invention is suitable for delivering a catalyst to the fluid in the first module, allowing a reaction catalyzed by the catalyst to proceed in the dwell module and, in the second module, separating the catalyst from the fluid. The catalyst is not subject to any particular restriction. Preferably, the catalyst is an enzyme (biocatalyst). Specifically, the method according to the invention is suitable for generating lactose-free milk. For this purpose, lactase is fed by way of the supply channel to the fluid in the first module which fluid, in this case, is lactose-containing milk. In the dwell module, the lactase converts the lactose contained in the fluid. In the second module, the lactase is separated out. When a filter unit with a first and a second filter medium is used, the lactose-free milk can be separated out as the permeate, whereby the lactase remains in the retentate.

According to a preferred embodiment of the present invention, the fluid which is conducted into the first module contains one or more products and possibly one or more contaminants.

The product or products is/are not subject to any particular restriction. Preferably, the product originates from a biotechnology process and is preferably produced by cells. According to the invention, "cells" include those that originate from humans, animals, plants, fungi, algae and bacteria. It is also preferred according to the invention that the product is a protein (e.g. an antibody), a virus and/or a vaccine.

The protein is not subject to any particular restriction and can be, for example, an enzyme or an antibody, the protein preferably being one or more antibodies. Specific examples of the antibody are immunoglobulin A, D, E, G, Y and mixtures thereof. The antibody can be, for example, recombinant, polyclonal or monoclonal.

Furthermore, the product can be a virus or a vaccine. The virus can be, for example, a modified virus, for example, a virus for gene therapy. Viruses for gene therapy invade cells of the patient intentionally infected with the virus and introduce their RNA and/or DNA into the cells. Vaccines can also comprise viruses and/or virus fragments. Both the product and also the contaminants described below in more detail can comprise viruses, whereby in this case, the product viruses are different from the contaminating viruses. It is possible, in principle, to separate the product viruses from the contaminating viruses, for example, by filtration (if the product viruses and the contaminating viruses have different sizes). Alternatively or in addition thereto, the contaminating viruses can in principle be selectively inactivated using the method according to the invention. For example, it is possible that the contaminating viruses are inactivated at a pH value at which the product viruses are not yet inactivated. In this way, just the contaminating viruses can be inactivated without inactivating the product viruses.

Any contaminants that are included are undesirable. They can possibly be separated from the product with the aid of filtration, for example, by way of the filter unit with the first and the second filter media. Alternatively or additionally thereto, the contaminants can possibly be inactivated, destroyed or otherwise rendered harmless by the method according to the invention. Specifically, the contaminants can be viruses (which are different from the desired product viruses possibly contained in the fluid). Examples of contaminants include—apart from viruses—salts, DNA, HCP (host cell protein), sugars and aggregates (e.g. protein aggregates).

For particular products (for example, pharmaceutical products such as monoclonal antibodies produced from cells), it can be required for reasons of hygiene to subject the fluid in which undesirable viruses can be contained as contaminants, to a virus inactivation. This virus inactivation can be achieved by a temporally limited modification in the pH value of the antibody-containing fluid, as described below.

In a preferred embodiment of the method according to the invention, in the first module, the pH value of the fluid is reduced and/or increased, whereby in the second module, the pH value of the fluid is increased and/or reduced. Such modifications of the pH value can be achieved by adding an acid and/or a base in the first and second modules. Thereby, the initial pH value of the fluid that is fed to the first module can correspond to or be different from the pH value of the fluid that is conducted away from the second module.

According to a preferred embodiment of the present invention, in the first module, the pH value of the fluid is reduced, whereas in the second module, the pH value of the fluid is increased. With this particular embodiment of the method according to the invention, any viruses contained in the fluid as contaminants can be inactivated. "Inactivated" means that the viruses are no longer capable of replication. Preferably, the pH value is reduced to a value from 2 to 6, particularly preferably from 3 to 5.

As described above, according to a preferred embodiment of the present invention, the first module is a membrane adsorber and the second module is the filter unit with the first and the second filter medium. In this case, after step (a) and before step (b), the method according to the invention preferably comprises the steps (a') feeding of a loading medium into the first module and (a") conducting away the loading medium from the first module. The loading medium can leave the device by way of the dwell module and the second module (filter unit). Preferably, a valve is mounted on the outlet of the membrane adsorber so that the loading medium can be conducted away therethrough without having to pass through the dwell module and the second module.

It is furthermore preferred that the fluid is a mixture which comprises and/or consists of an aqueous buffer and one or more products and possibly one or more contaminants. According to another preferred embodiment of the method according to the invention, the fluid that is fed to the first module contains an aqueous buffer, one or more monoclonal antibodies and possibly viruses and possibly one or more contaminants.

According to the invention, by the adjustment of the volumetric flow rate at the inlet and at the outlet of the retentate channel, the volume of the fluid and thus the concentration of the constituents contained therein can be adjusted. Preferably, the ratio of the volumetric flow rate of the fluid fed in in step (ii) to the volumetric flow rate of the fluid conducted away in step (iii) is from 1:10 to 10:1. Furthermore, the ratio of the volumetric flow rate of the supply medium fed in in step (i) to the volumetric flow rate of the fluid fed in in step (ii) is preferably from 1:1000 to 10:1.

In a preferred embodiment of the method, the supply medium is fed in at a pressure from 0.1 to 4 bar. It is particularly preferred that the supply medium be fed in at a pressure that is greater than the retentate outlet pressure. Furthermore, the pressure difference between the retentate channel and the permeate channel is preferably from 0.1 to 1.5 bar.

According to a preferred embodiment of the present invention, the dwell time of the fluid in the dwell module is from 1 minute to 24 hours, preferably from 5 minutes to 2 hours, more preferably from 10 minutes to 1 hour.

According to a preferred embodiment of the present invention, the first module is a first filter unit and the second module is a second filter unit, step (b) comprising the following steps: (b-i) feeding the supply medium into the inlet of the first filter unit for the supply medium; (b-ii) feeding the fluid into the inlet of the first filter unit for the fluid; (b-iii) conducting away the fluid from the outlet of the first filter unit for the fluid; and (b-iv) conducting away the permeate from the outlet of the first filter unit for the permeate, and step (c) comprising the following steps: (c-i) feeding the supply medium into the inlet of the second filter unit for the supply medium; (c-ii) feeding the fluid into the inlet of the second filter unit for the fluid; (c-iii) conducting away the fluid from the outlet of the second filter unit for the fluid; and conducting away the permeate from the outlet of the second filter unit for the permeate. The fluid conducted away in step (b-iii) is fed into the inlet of the dwell module. The fluid conducted away from the dwell module is fed in step (c-ii) into the inlet of the second filter unit for the fluid.

The method according to the invention is preferably operated continuously, that is to say, with constant/continuous addition of the supply medium and the fluid, as a result of which a particularly efficient and economical method for repeatedly modifying the concentration of a fluid can be provided. According to the invention, a "continuous" method for repeatedly modifying the concentration of a fluid can be understood to be a method in which both the supply medium and also the fluid are continuously fed in.

BRIEF DESCRIPTION OF THE DRAWINGS

FIG. 1 shows an embodiment configured to adjust a pH value of a fluid, while FIG. 2 shows an embodiment configured for virus inactivation of a fluid that contains monoclonal antibodies and for removing contaminants.

DETAILED DESCRIPTION

Figure 1:
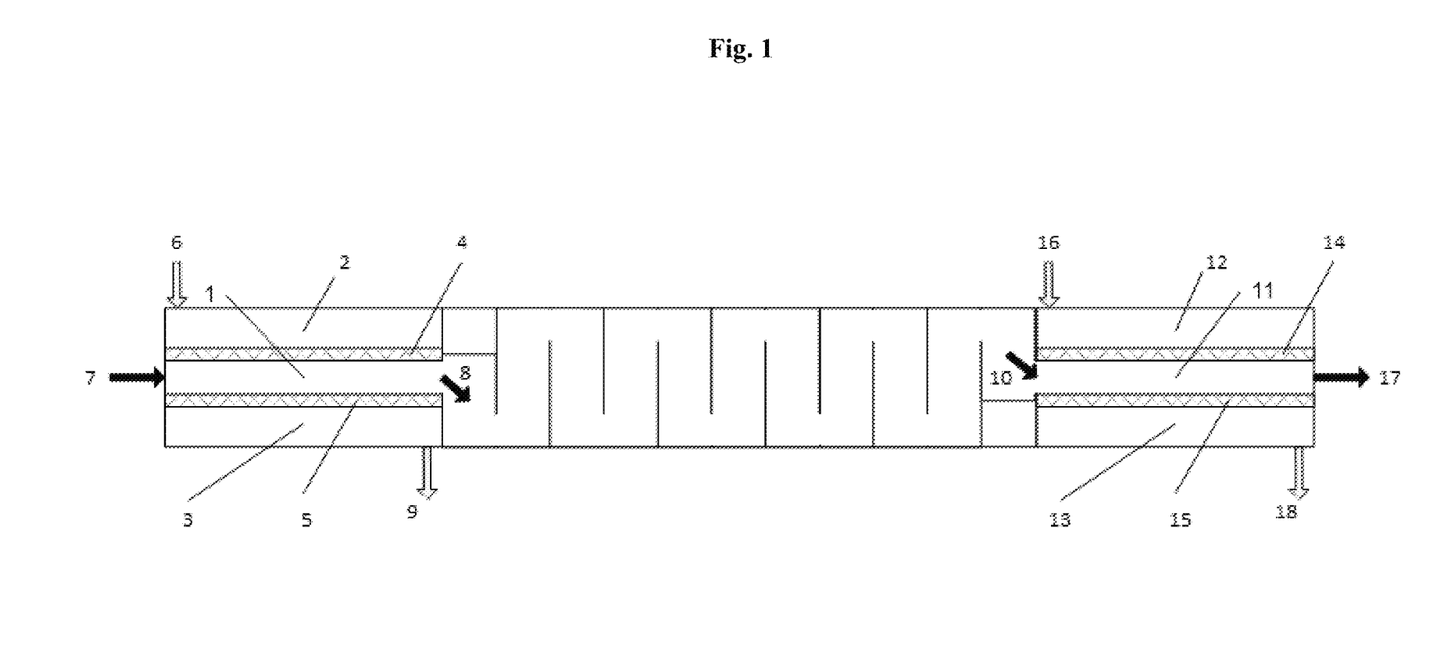
FIGS. 1 and 2 show exemplary embodiments of the device according to the invention and additionally illustrate embodiments of the method according to the invention.

FIG. 1 shows an exemplary embodiment of the device according to the invention and/or of the method according to the invention. The device of this embodiment is suitable, for example, for adjusting the pH value of a fluid. The device has three modules: a first module (left) which transitions directly into a dwell module (center), which in turn transitions directly into a second module (right).

In a first aspect, the present invention relates to a device for repeatedly modifying the composition of a fluid, comprising a first module (19) for modifying the composition of the fluid, a second module (21) for modifying the composition of the fluid and a dwell module (20) with an inlet (8) and an outlet (10). The first module (19) is connected in a fluid-conducting manner to the inlet (8) of the dwell module (20) and the outlet (10) of the dwell module (20) is connected in a fluid-conducting manner to the second module (21). The first module (19) or the second module (21) is a filter unit or the first module (19) is a first filter unit and the second module (21) is a second filter unit. The filter unit and/or filter units each has/have at least one supply channel (2, 12), at least one first filter medium (4, 14), at least one retentate channel (1, 11), at least one second filter medium (5, 15) and at least one permeate channel (3, 13), arranged so that the first filter medium (4, 14) delimits the supply channel (2, 12) and the retentate channel (1, 11) from one another and the second filter medium (5, 15) delimits the retentate channel (1, 11) and the permeate channel (3, 13) from one another, the supply channel (2, 12) is connected in a fluid-conducting manner to at least one inlet (6, 16, 24, 27) for a supply medium, the retentate channel (1, 11) is connected in a fluid-conducting manner to at least one inlet (7, 10, 23) for the fluid and to at least one outlet (8, 17, 23) for the fluid, and the permeate channel (3, 13) is connected in a fluid-conducting manner to at least one outlet (9, 18, 25, 28) for a permeate.

As shown in FIG. 1, each of the first and second modules is a filter unit. Each of the filter units has a retentate channel (1, 11), a supply channel (2, 12), a permeate channel (3, 13), a first filter medium (4, 14) and a second filter medium (5, 15). The first filter medium (4, 14) separates the supply channel (2, 12) from the retentate channel (1, 11) and the second filter medium (5, 15) separates the retentate channel (1, 11) from the permeate channel (3, 13).

By way of the inlet (7, 10) of the retentate channel (1, 11) of the filter unit of the first module (first filter unit) and/or of the filter unit of the second module (second filter unit), the fluid is fed to the first and/or the second module. A supply medium is fed in by way of the inlet (6, 16) of the supply channel (2, 12). The supply medium passes through the first filter medium (4, 14) and is thus brought into contact with the fluid in the retentate channel (1, 11). According to the invention, the same supply medium can be fed into the first and second filter units, whereby supply media with different compositions are preferably used. By way of the supply channel (2, 12), a fluid is fed in, which changes the composition of the fluid in the retentate, e.g. its pH value. In the case of the virus inactivation, an acidic aqueous solution, for example, a solution of citric acid in water, can be fed in as the first supply medium by way of the inlet (6) of the supply channel of the first filter unit, in order to bring about a reduction in the pH value of the fluid in the retentate channel (1). A buffer solution (e.g. an aqueous phosphate buffer) or a basic aqueous solution can be fed in as the second supply medium by way of the inlet (16) of the supply channel of the second filter unit, so that the pH value of the fluid in the retentate channel (11) of the second filter unit is increased.

The properties of the second filter medium (5, 15) can be selected so that only particular components of the fluid pass through the second filter medium (5, 15) in order thereby to achieve a desired separation effect. In particular, if the fluid contains one or more antibodies as the product, an ultrafiltration membrane with a pore size from 2 to 100 nm can be used as the second filter medium (5, 15) so that the antibody/antibodies remain in the fluid and do not pass into the permeate channel (3, 13). Furthermore, by using an ultrafiltration membrane with a pore size from 2 to 100 nm as the second filter medium (5, 15), a vaccine contained in the fluid as the product can be held back by the ultrafiltration membrane. Constituents of the fluid which are able to pass through the second filter medium (5, 15) (e.g. contaminants) pass through the second filter medium (5, 15) at least partially or completely and are conducted away by way of the permeate channel (3, 13) and its outlet (9, 18) as the permeate. Thereby, in addition to a repeated modification of the composition of the fluid, contaminants can be separated out.

By way of the outlet (8) of the retentate channel (1) of the first filter unit and/or the inlet (8) of the dwell module, the fluid is fed from the first module to the dwell module. The dwell module has a plurality of deflector plates which define a fluid path through which the fluid flows. Through the design of the fluid path (path length, flow velocity of the fluid and the surface area of the path), the dwell time of the fluid in the dwell module can be adjusted. Thus, for example, in the case of the virus inactivation during this dwell time, the viruses are subjected to the adjusted properties of the fluid (for example, a low pH value) in the first module, so that a complete inactivation of the viruses can be ensured. The fluid leaves the dwell module by way of its outlet (10) and/or the inlet (10) of the retentate channel of the second filter unit.

Figure 2:
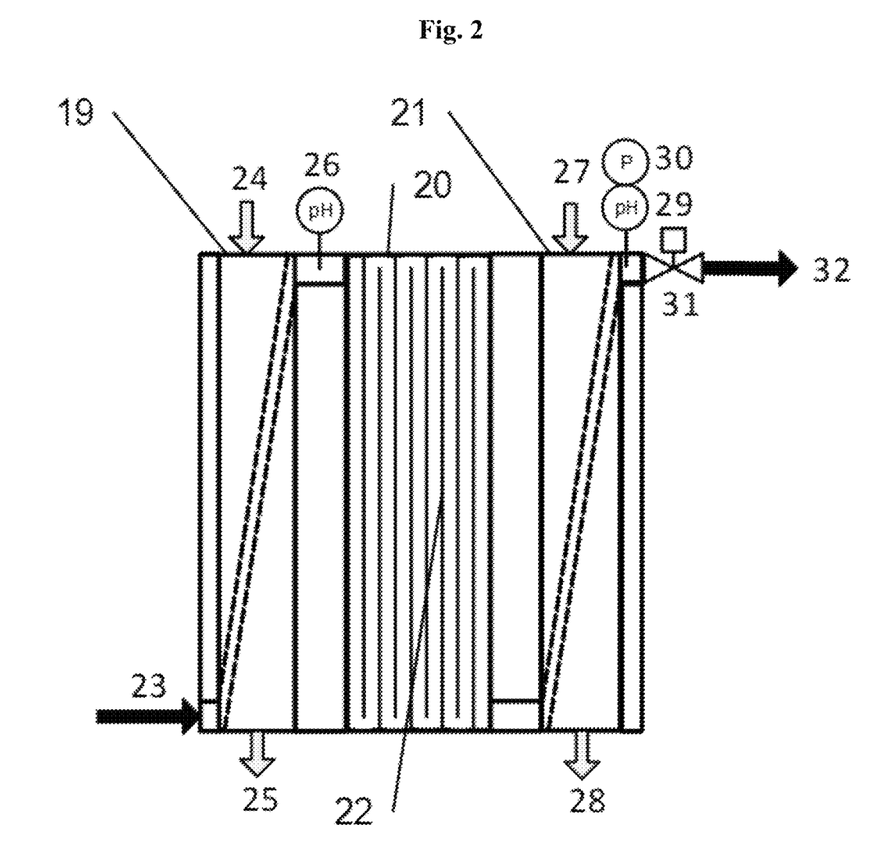

FIG. 2 shows a further exemplary embodiment of the device according to the invention and/or of the method according to the invention. The embodiment shown in FIG. 2 is also suitable for the virus inactivation and, in particular, for virus inactivation of a fluid which contains monoclonal antibodies, while simultaneously removing contaminants from the fluid (by way of the permeate).

In this embodiment, the fluid is introduced, by the use of a pressure gradient, into the retentate channel and simultaneously, by the use of a pressure gradient between the retentate channel and the permeate channel, a filtration takes place in the permeate channel. The pressure gradient can be controlled, for example, by a valve on the outlet of the retentate channel of the first module (19) and/or the first filter unit (19) and/or by a valve on the outlet of the retentate channel of the second module (21) and/or of the second filter unit (21) and/or by a valve on the outlet of the dwell module (20).

The fluid can be introduced from a chromatography step possibly arranged upstream, with the aid of a pump (not shown in FIG. 2) into the inlet (23) of the retentate channel of the first filter unit (19). Through the selection of a suitable separating boundary of the second filter medium of the filter units (19, 21), a product/target molecule contained in the fluid (e.g. a monoclonal antibody) can be retained without passing through the second filter medium.

By way of the inlet (24) of the supply channel, a supply medium (for example, an aqueous citric acid solution) is introduced into the supply channel and thereby by way of the first filter medium into the retentate channel. The quantity fed in is controlled by use of the pH value measured by a pH sensor (26). The pH value can be reduced, for example, from 7 to 3.5.

At the same time, in this preferred embodiment, by use of a pressure gradient between the retentate channel and the permeate channel, a filtration takes place in the permeate channel. The volumetric flow rate at the outlet (25) of the permeate channel is the same size in the exemplary embodiment as the volumetric flow rate of the quantity of supply medium fed to the supply channel. Thus, the concentration of the constituents remaining in the fluid, and the volume of the fluid, remain constant.

Preferably, an ultrafilter with a pore size in the region from 2 to 100 nm is used as the second filter medium. The first and the second filter medium do not have to have the same pore size and/or material properties. Preferably, the transmembrane pressure between the retentate channel and the permeate channel is from 0.1 to 1.5 bar. The transmembrane pressure between the supply channel and the retentate channel is preferably from 0.01 to 0.4 bar.

In the exemplary embodiment shown in FIG. 2, the dwell module is connected directly to the first module/the first filter unit. In the dwell module of this exemplary embodiment, by use of the arrangement of deflector films (22) and spacers (e.g. textile materials; not shown in FIG. 2) in stacks, a channel is formed. This channel forms a fluid path. In accordance with common flat filter constructions which are known to persons skilled in the art, the stacks can be combined, for example, by pressing, overmolding or injection molding.

In the second module of the embodiment shown in FIG. 2, similarly to the first module, for example a phosphate-buffered salt solution with a pH value of 7 is introduced by way of the inlet (27) of the supply channel into the supply channel and thereby by way of the first filter medium into the retentate channel. The quantity fed in can be adjusted on the basis of the pH value. The pH value can be measured with a sensor (29). The pH value can be increased, for example, from 3.5 to a value of 7.

With the aid of a pressure sensor (30) and a valve (31), the filtration pressure and the output volumetric flow rate can be adjusted.

In the exemplary embodiment shown in FIG. 2, in the case of a (perfusion) process with a batch volume of 50 l, the area of the filter medium of the first and the second module can each be 1.5 m² and the overall channel length (fluid path length) of the dwell module can be 2 m, provided that a continuous volumetric flow rate of approximately 35 ml/min for a total duration of 24 h is assumed for the (perfusion) process. The dwell time of the fluid in the dwell module at a pH value of 3.5 would be approximately 42 minutes in this case.

REFERENCE SIGNS 1, 11 Retentate channel
2, 12 Supply channel
3, 13 Permeate channel
4, 14 First filter medium
5, 15 Second filter medium
6, 16, 24, 27 Inlet for supply medium
7, 10, 23 Inlet of the retentate channel for the fluid
8 Inlet of the dwell module
8, 17,32 Outlet for the fluid
9, 18, 25, 28 Outlet for the permeate
10 Outlet of the dwell module
19 First module
20 Dwell module
21 Second module
22 Deflector films
26, 29 pH sensor
30 Pressure sensor
31 Valve The present invention is explained further with the following reference example, but is not limited thereto.

Representative Example

The following starting materials were provided.
Feed liquid (fluid): 20 g/l bovine serum albumin (BSA) in 0.1 M citrate buffer with a pH value of 3.5 Supply liquid: 0.1 M citrate buffer with a pH value of 2
Aim: the rebuffering (buffer exchange) of the feed liquid and a pH value reduction from pH 3.5 to pH 2.5 with the aid of supply liquid and an incubation in a dwell module.

As the first module, a first filter unit with first and second filter media of the ultrafine membrane type made from polyethersulfone with a MWCO (molecular weight cut-off) of 10 kDa was used. The total membrane area of the first filter medium was 0.027 m². A textile material for thorough mixing of the retentate was introduced into the retentate channel of the first filter unit.

In order to monitor the process, the transmembrane pressure (TMP) was measured. Furthermore, the protein concentration of the retentate at the retentate outlet was measured to determine when the concentration of BSA in the retentate corresponded to that in the feed liquid and the process was in a state of equilibrium. Furthermore, the pH value of the retentate at the retentate outlet was measured to determine when the pH value of the retentate corresponded to the target setpoint of pH 2.5 and the process was in a state of equilibrium. The volumetric flow rates of the feed liquid, the supply liquid and the retentate were 6 ml/min, 6.5 ml/min and 6 ml/min, respectively.

Figure 3:
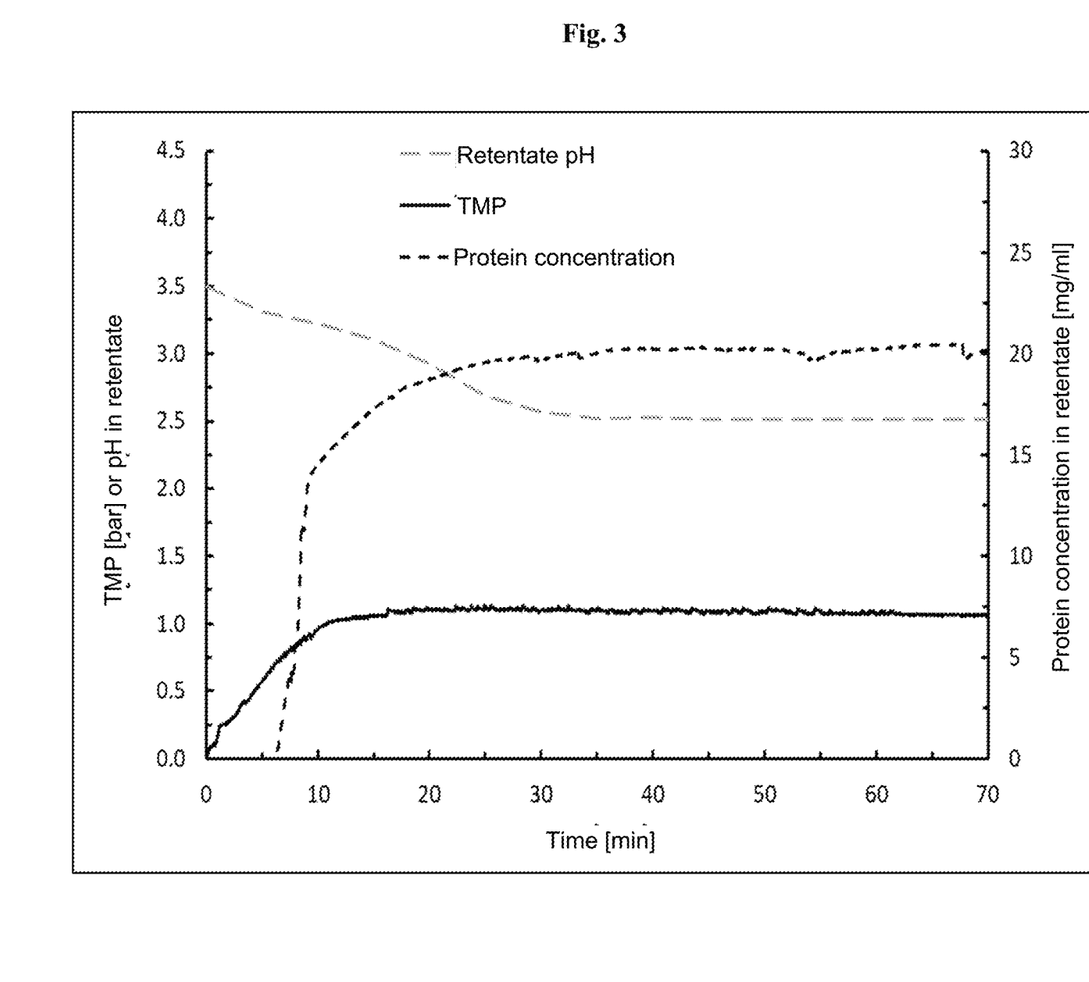
FIG. 3 shows results of a representative example performed in accordance with the invention.

FIG. 3 shows that an equilibrium state was reached for all the parameters TMP, pH and protein concentration. The required pH value of 2.5 in the retentate was achieved. Due to the textile material in the retentate channel, the retentate was optimally mixed.

The retentate was subsequently fed into a dwell module consisting of 50 successive channels as shown schematically in FIG. 2. The channels were each subdivided by a deflector film. The height, breadth and length of each channel were respectively approximately 0.41 mm, 30 mm and 150 mm. This resulted in a total length of the fluid path defined by the dwell module of approximately 7500 mm. The dwell time of the fluid in the dwell module was determined by measuring the time from the entry of the liquid into the inlet until the emergence of the liquid from the outlet. With an inlet volumetric flow rate into the dwell module of 6 ml/min, a dwell time of 15.5 min was measured.

What is claimed is:
1. A device for repeatedly modifying a composition of a fluid, comprising:
a first module for modifying the composition of the fluid, a second module for modifying the composition of the fluid and a dwell module with an inlet and an outlet, wherein the first module is connected in a fluid-conducting manner to the inlet of the dwell module and the outlet of the dwell module is connected in a fluid-conducting manner to the second module,
wherein at least one of the first module and the second module is a filter unit,
wherein the filter unit has:
at least one supply channel,
at least one first filter medium,
at least one retentate channel,
at least one second filter medium, and
at least one permeate channel,
arranged so that the first filter medium delimits the supply channel and the retentate channel from one another, and the second filter medium delimits the retentate channel and the permeate channel from one another,
wherein the supply channel is connected in a fluid-conducting manner to at least one inlet for a supply medium,
wherein the retentate channel is connected in a fluid-conducting manner to at least one inlet for the fluid and to at least one outlet for the fluid,
wherein the permeate channel is connected in a fluid-conducting manner to at least one outlet for a permeate, and wherein either:
(i) the dwell module defines a coherent volume internally subdivided by at least one subdividing element forming a non-linear fluid path, or
(ii) the dwell module comprises a plurality of flow channels arranged in parallel to one another and all connected in a fluid-conducting manner to the inlet of the dwell module and in a fluid-conducting manner to the outlet of the dwell module.

2. The device as claimed in claim 1,
wherein the first module is the filter unit and the second module is a second filter unit, and
wherein the second filter unit has:
at least one supply channel,
at least one first filter medium,
at least one retentate channel,
at least one second filter medium, and
at least one permeate channel,
arranged so that the first filter medium delimits the supply channel and the retentate channel from one another, and the second filter medium delimits the retentate channel and the permeate channel from one another.

3. The device as claimed in claim 1,
wherein the first module or the second module is a static mixer.

4. The device as claimed in claim 3,
wherein the first module is the static mixer and the second module is the filter unit.

5. The device as claimed in claim 1,
wherein the first module is the filter unit and the second module is a further filter, and
wherein the further filter comprises a single filter medium and/or is selected from the group consisting essentially of: a sterile filter; a dead-end filter; a filter consisting essentially of a supply channel, a single filter medium and a retentate channel; and a filter consisting essentially of a retentate channel, a single filter medium and a permeate channel.

6. The device as claimed in claim 1,
wherein the first module comprises a membrane adsorber or a chromatography module, and the second module is the filter unit.

7. The device as claimed in claim 6,
wherein the membrane adsorber is laden with a product and comprises an outlet controlled by a valve.

8. A method for repeatedly modifying a composition of a fluid, comprising:
(a) providing the device as claimed in claim 1;
(b) feeding the fluid into the first module; and
(c) conducting the fluid out of the second module,
wherein said step (b) and/or said step (c) comprise/comprises the following steps:
(i) feeding the supply medium into the inlet for the supply medium;
(ii) feeding the fluid into the inlet for the fluid;
(iii) conducting the fluid out through the outlet for the fluid; and
(iv) conducting the permeate out through the outlet for the permeate.

9. The method as claimed in claim 8,
wherein the fluid which is fed into the first module contains at least one product.

10. The method as claimed in claim 9,
wherein the fluid which is fed into the first module additionally contains at least one contaminant.

11. The method as claimed in claim 8,
wherein a pH value of the fluid is reduced and/or increased in the first module, and
wherein, in the second module, the pH value of the fluid is increased and/or reduced.

12. The method as claimed in claim 11,
wherein the pH value of the fluid is reduced in the first module and wherein the pH value of the fluid is increased in the second module.

13. The method as claimed in claim 8,
wherein a dwell time of the fluid in the dwell module is from 1 minute to 24 hours.

14. The method as claimed in claim 8,
wherein the first module is the first filter unit and the second module is the second filter unit,
wherein said step (b) comprises the following steps:
(b-i) feeding the supply medium into the inlet of the first filter unit for the supply medium;
(b-ii) feeding the fluid into the inlet of the first filter unit for the fluid;
(b-iii) conducting the fluid out of the first filter unit through the outlet of the first filter unit for the fluid; and
(b-iv) conducting the permeate out of the first filter unit through the outlet of the first filter unit for the permeate, and
step (c) comprises the following steps:
(c-i) feeding the supply medium into the inlet of the second filter unit for the supply medium;
(c-ii) feeding the fluid into the inlet of the second filter unit for the fluid;
(c-iii) conducting the fluid out of the second filter unit through the outlet of the second filter unit for the fluid; and
(c-iv) conducting the permeate out of the second filter unit through the outlet of the second filter unit for the permeate.

15. The method as claimed in claim 11, wherein the fluid comprises a virus and wherein the virus is inactivated prior to said step (c) of conducting the fluid out of the second module.

16. The device as claimed in claim 1,
wherein the at least one supply channel, the at least one retentate channel, the at least one permeate channel, the at least one first filter medium, and the at least one second filter medium are configured as a cross-flow filter module.

17. The device as claimed in claim 1,
wherein the dwell module comprises a fluid path having one or more meandering channels and/or one or more spiral shaped channels extending in a longitudinal direction.

18. The device as claimed in claim 1,
wherein the at least one subdividing element comprises at least one of: at least one deflector plate, at least one deflector film, and a plurality of deflector films mutually separated by respective spacers.

* * * * *